United States Patent
Luciano et al.

(10) Patent No.: US 8,730,321 B2
(45) Date of Patent: May 20, 2014

(54) AUTOMATIC ALIGNMENT OF A CONTRAST ENHANCEMENT SYSTEM

(75) Inventors: Vincent Luciano, Farmingville, NY (US); Fred Wood, Medford, NY (US)

(73) Assignee: AccuVein, Inc.

( * ) Notice: Subject to any disclaimer, the term of this patent is extended or adjusted under 35 U.S.C. 154(b) by 1069 days.

(21) Appl. No.: 12/215,713

(22) Filed: Jun. 27, 2008

(65) Prior Publication Data
US 2009/0002488 A1 Jan. 1, 2009

Related U.S. Application Data

(60) Provisional application No. 60/937,618, filed on Jun. 28, 2007.

(51) Int. Cl.
*H04N 7/18* (2006.01)

(52) U.S. Cl.
USPC ............. 348/135; 348/136; 348/137; 353/10; 353/28; 345/32; 359/15

(58) Field of Classification Search
USPC ......... 348/135, 136, 137; 353/10, 28; 345/32; 359/15
See application file for complete search history.

(56) References Cited

U.S. PATENT DOCUMENTS

| | | |
|---|---|---|
| 2,289,149 A | 5/1976 | Siemens |
| 4,265,227 A | 5/1981 | Ruge |
| 4,312,357 A | 1/1982 | Andersson et al. |
| 4,495,949 A | 1/1985 | Stoller |
| 4,502,075 A | 2/1985 | DeForest et al. |
| 4,619,249 A | 10/1986 | Landry |
| 4,817,622 A | 4/1989 | Pennypacker et al. |
| RE33,234 E | 6/1990 | Landry |
| 5,214,458 A | 5/1993 | Kanai |
| 5,261,581 A | 11/1993 | Harden |
| 5,406,070 A | 4/1995 | Edgar et al. |
| 5,519,208 A | 5/1996 | Esparza et al. |
| 5,541,820 A | 7/1996 | McLaughlin |
| 5,603,328 A | 2/1997 | Zucker et al. |
| 5,608,210 A | 3/1997 | Esparza et al. |
| 5,631,976 A | 5/1997 | Bolle et al. |
| 5,678,555 A | 10/1997 | O'Connell |
| 5,772,593 A | 6/1998 | Hakamata |
| 5,836,877 A | 11/1998 | Zavislan |
| 5,860,967 A | 1/1999 | Zavislan et al. |
| 5,969,754 A | 10/1999 | Zeman |
| 5,988,817 A | 11/1999 | Mizushima et al. |
| 5,995,856 A | 11/1999 | Mannheimer et al. |
| 6,032,070 A | 2/2000 | Flock et al. |
| 6,056,692 A | 5/2000 | Schwartz |
| 6,061,583 A | 5/2000 | Ishihara et al. |

(Continued)

FOREIGN PATENT DOCUMENTS

| | | |
|---|---|---|
| FR | 2289149 | 5/1976 |
| GB | 1507329 | 4/1978 |

(Continued)

*Primary Examiner* — Thuong Nguyen
(74) *Attorney, Agent, or Firm* — Thomas A. O'Rourke; Bodner & O'Rourke, LLP

(57) ABSTRACT

An apparatus and method for insuring the proper alignment of a detected vein pattern and a projected vein pattern are disclosed. The apparatus enhances the visual appearance of veins so that an error that can lead to improper patient care or injury can be avoided.

12 Claims, 3 Drawing Sheets

(56) References Cited

U.S. PATENT DOCUMENTS

| | | | |
|---|---|---|---|
| 6,135,599 A | 10/2000 | Fang | |
| 6,149,644 A | 11/2000 | Xie | |
| 6,230,046 B1 | 5/2001 | Crane et al. | |
| 6,251,073 B1 | 6/2001 | Imran et al. | |
| 6,263,227 B1 | 7/2001 | Boggett et al. | |
| 6,334,850 B1 | 1/2002 | Amano et al. | |
| 6,424,858 B1 | 7/2002 | Williams | |
| 6,463,309 B1 | 10/2002 | Ilia | |
| 6,464,646 B1 | 10/2002 | Shalom et al. | |
| 6,542,246 B1 | 4/2003 | Toida | |
| 6,556,854 B1 | 4/2003 | Sato et al. | |
| 6,556,858 B1 | 4/2003 | Zeman | |
| 6,690,964 B2 | 2/2004 | Bieger et al. | |
| 6,702,749 B2 | 3/2004 | Paladini et al. | |
| 6,782,161 B2 | 8/2004 | Barolet et al. | |
| 6,882,875 B1 | 4/2005 | Crowley | |
| 6,889,075 B2 | 5/2005 | Marchitto et al. | |
| 6,923,762 B1 | 8/2005 | Creaghan, Jr. | |
| 6,980,852 B2 | 12/2005 | Jersey-Willuhn et al. | |
| 7,158,660 B2 | 1/2007 | Gee, Jr. et al. | |
| 7,225,005 B2 | 5/2007 | Kaufman et al. | |
| 7,239,909 B2 | 7/2007 | Zeman | |
| 7,247,832 B2 | 7/2007 | Webb | |
| 7,283,181 B2 | 10/2007 | Allen | |
| 7,333,213 B2 | 2/2008 | Kempe | |
| 7,359,531 B2 | 4/2008 | Endoh et al. | |
| 7,608,057 B2 | 10/2009 | Woehr et al. | |
| 8,078,263 B2 * | 12/2011 | Zeman et al. | 600/473 |
| 8,320,998 B2 | 11/2012 | Sato | |
| 2001/0006426 A1 * | 7/2001 | Son et al. | 359/15 |
| 2002/0118338 A1 | 8/2002 | Kohayakawa | |
| 2003/0018271 A1 | 1/2003 | Kimble | |
| 2003/0156260 A1 * | 8/2003 | Putilin et al. | 353/10 |
| 2004/0171923 A1 | 9/2004 | Kalafut et al. | |
| 2005/0017924 A1 | 1/2005 | Utt et al. | |
| 2005/0043596 A1 | 2/2005 | Chance | |
| 2005/0113650 A1 | 5/2005 | Pacione et al. | |
| 2005/0135102 A1 | 6/2005 | Gardiner et al. | |
| 2005/0141069 A1 | 6/2005 | Wood et al. | |
| 2005/0143662 A1 | 6/2005 | Marchitto et al. | |
| 2005/0157939 A1 | 7/2005 | Arsenault et al. | |
| 2005/0161051 A1 | 7/2005 | Pankratov et al. | |
| 2005/0174777 A1 | 8/2005 | Cooper et al. | |
| 2005/0175048 A1 | 8/2005 | Stern et al. | |
| 2005/0185539 A1 * | 8/2005 | Shimano et al. | 369/44.37 |
| 2005/0215875 A1 | 9/2005 | Khou | |
| 2005/0281445 A1 | 12/2005 | Marcotte et al. | |
| 2006/0007134 A1 * | 1/2006 | Ting | 345/156 |
| 2006/0103811 A1 | 5/2006 | May et al. | |
| 2006/0129037 A1 | 6/2006 | Kaufman et al. | |
| 2006/0129038 A1 | 6/2006 | Zelenchuk et al. | |
| 2006/0173351 A1 | 8/2006 | Marcotte et al. | |
| 2006/0232660 A1 | 10/2006 | Nakajima et al. | |
| 2006/0253010 A1 | 11/2006 | Brady et al. | |
| 2006/0271028 A1 | 11/2006 | Altshuler et al. | |
| 2007/0016079 A1 | 1/2007 | Freeman et al. | |
| 2007/0115435 A1 | 5/2007 | Rosendaal | |
| 2007/0161909 A1 * | 7/2007 | Goldman et al. | 600/476 |
| 2007/0176851 A1 * | 8/2007 | Willey et al. | 345/32 |
| 2008/0147147 A1 | 6/2008 | Griffiths et al. | |
| 2008/0177184 A1 * | 7/2008 | Goldman et al. | 600/476 |
| 2008/0194930 A1 | 8/2008 | Harris et al. | |
| 2008/0197170 A1 * | 8/2008 | Prince | 228/103 |
| 2008/0252882 A1 * | 10/2008 | Kesterson | 356/300 |
| 2008/0278445 A1 * | 11/2008 | Sweetser et al. | 345/158 |
| 2009/0220415 A1 * | 9/2009 | Shachaf et al. | 424/1.11 |
| 2009/0268208 A1 * | 10/2009 | Ertl | 356/479 |
| 2010/0020078 A1 * | 1/2010 | Shpunt | 345/420 |
| 2010/0051808 A1 | 3/2010 | Zeman et al. | |
| 2010/0087787 A1 | 4/2010 | Woehr et al. | |
| 2010/0177184 A1 | 7/2010 | Berryhill et al. | |

FOREIGN PATENT DOCUMENTS

| | | |
|---|---|---|
| JP | 08023501 A | 1/1996 |
| JP | 2002328428 A | 11/2002 |
| JP | 2004/237051 | 8/2004 |
| JP | 2004237051 | 8/2004 |
| WO | WO 94/22370 | 10/1994 |
| WO | WO 96/39925 | 12/1996 |
| WO | WO 9826583 | 6/1998 |
| WO | WO 01/82786 | 11/2001 |
| WO | WO 03/009750 | 2/2003 |
| WO | WO 2007/078447 | 7/2007 |

* cited by examiner

AUTOMATIC ALIGNMENT OF A CONTRAST ENHANCEMENT SYSTEM

This application claims priority on U.S. Provisional Application Ser. No. 60/937,618 filed Jun. 28, 2007 the disclosures of which are incorporated herein by reference.

SUMMARY OF THE INVENTION

An apparatus and method for insuring the proper alignment of a detected vein pattern and a projected vein pattern in a apparatus that enhances the visual appearance of veins so that an error that can lead to improper patient care or injury can be avoided.

BACKGROUND OF THE INVENTION

It is known in the art to use an apparatus to enhance the visual appearance of the veins and arteries in a patient to facilitate insertion of needles into those veins and arteries as well as other medical practices that require the identification of vein and artery locations. Such a system is described in U.S. Pat. Nos. 5,969,754 and 6,556,858 incorporated herein by reference as well as publication entitled "The Clinical Evaluation of Vein Contrast Enhancement". Luminetx is currently marketing such a device under the name "Veinviewer Imaging System" and information related thereto is available on their website, which is incorporated herein by reference.

The Luminetx Vein Contrast Enhancer (hereinafter referred to as LVCE) utilizes a light source for flooding the region to be enhanced with near infrared light generated by an array of LEDs. A CCD imager is then used to capture an image of the infrared light reflected off the patient. The resulting captured image is then digitally enhanced and then projected by a visible light projector onto the patient in a position that must be closely aligned with position of the captured image. The practitioner uses this projected image to determine the position in which to insert a needle. Should the image be misaligned, the patient can be injured.

DETAILED DESCRIPTION OF THE INVENTION

Figure 1:
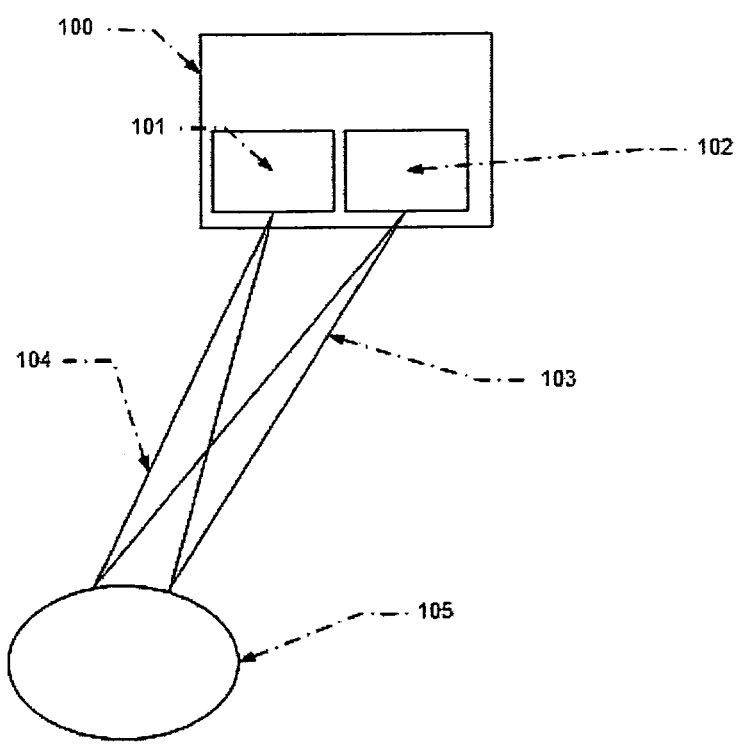
FIG. 1 shows an embodiment of a vein contrast enhancer.

As shown in FIG. 1, a typical embodiment of a vein contrast enhancer (VCE) 100 contains a camera 101 which is used to capture an image of a patient's body 105, a processing system (not shown) that enhances the image captured by the camera to highlight the positions of veins, and a projector 102 that shows an image of the enhanced vein pattern back onto the patient's body 105. Since the camera and projector are physically separate devices they reach the patient's body from different source points along different paths 103, 104. In some embodiments, the paths are made coaxial within the body of the VCE, however at some point the paths are separate since the devices (camera and projector) are physically separate devices. Since the purpose of a VCE is to allow the practitioner to insert a needle into the highlighted vein, it is critically important that the projected image and the actual vein location be aligned. Typically this alignment is done as a separate step in the use of the VCE. A card with a known pattern is placed with the viewing/projecting field of the VCE. This card has a florescent material applied to it so that when it is struck by green light, it emits infrared light that can be seen by the camera. This image is used to align the VCE.

This invention describes methods for achieving this alignment without requiring the operator to take a separate step.

Figure 2:
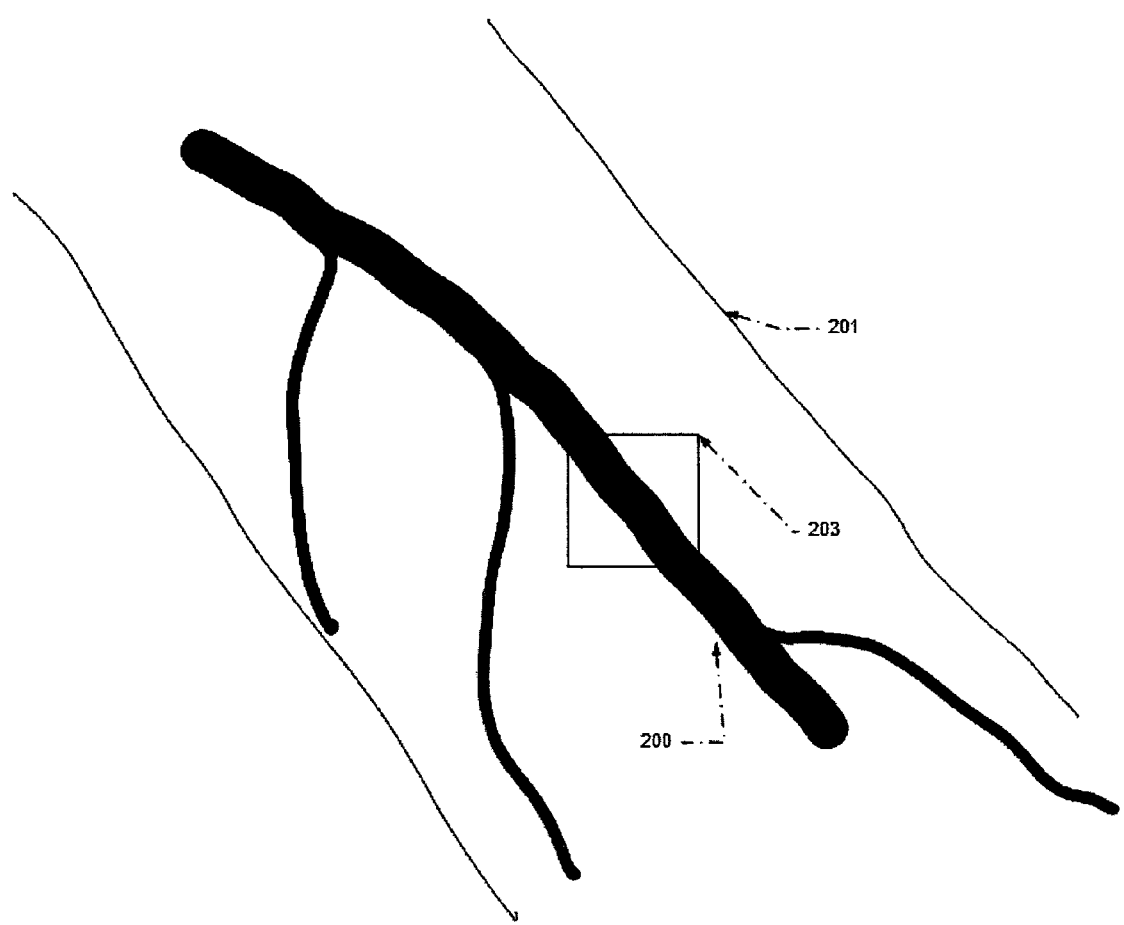
FIG. 2 is a representation of a patient's arm.
Figure 3:
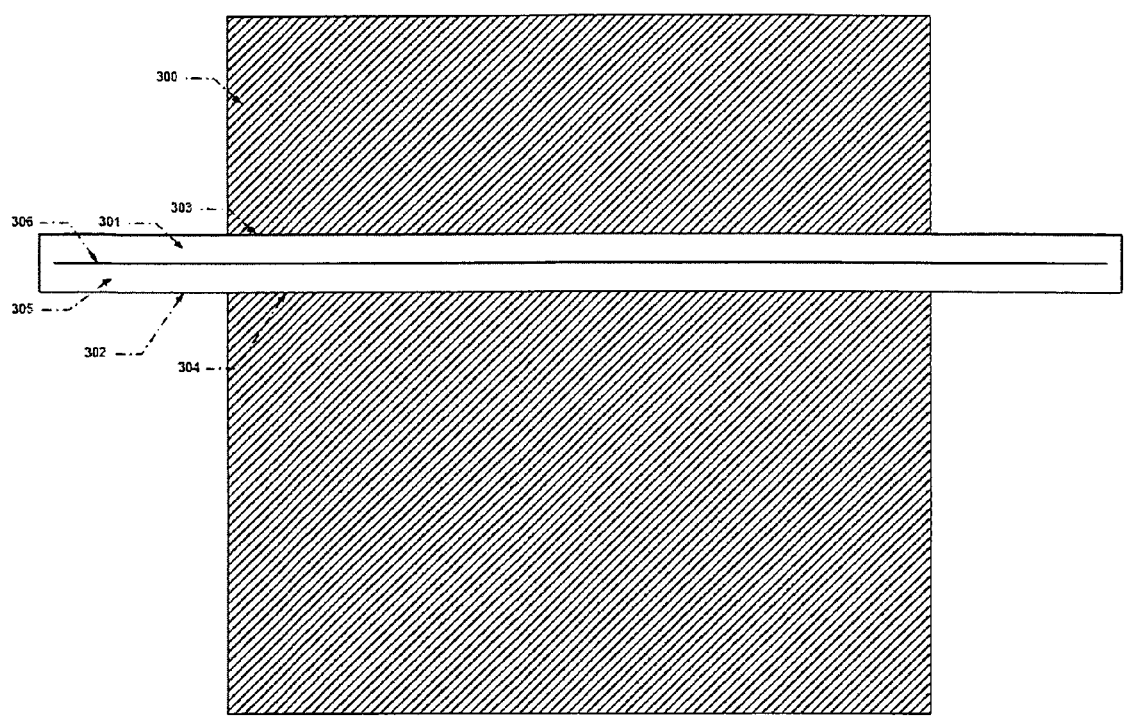
FIG. 3 shows an embodiment of a laser contrast enhancer

Referring to FIG. 2, a representation of the patient's arm 201 is shown along with several veins. A bounding box is shown around a single vein 200. In FIG. 3, a schematic representation of the bounded area of the single vein is shown 305. Typically, the enhancement image will light up the area around the vein and will be dark on the vein. When properly aligned, the bright part of the image 300 will have edges that properly align with the edges of the vein 303, 304. As previously described, the VCE will typically have an alignment mode wherein a known pattern, typically presented on an alignment card, will be placed in front of the VCE and an alignment will be performed. This alignment can either be automatically performed by the VCE or manually performed by the operator. The weakness of this kind of implementation is that it relies on the expectation that the alignment will be maintained over time. If the alignment should shift, patient injury can occur.

In a typical VCE, an infrared light source and a camera that is sensitive only to infrared light is used to detect the vein position. Furthermore, the projected image is often green in color to insure that the light from the projector is ignored since the camera is sensitive only to light near the infrared region. This selectivity can be implemented either with filters or with selectively sensitive camera elements.

Referring back to FIG. 3, in a typical LCE, the camera, by design, is blind to the projected light. In our invention, the camera is by design, able to selectively see the projected light. In a preferred embodiment, a multi-color capable projector is used. As usual, green is used to fill the area outside of the vein 300. That green projection goes to the edges of the vein position 303, 304 and the vein area itself is left dark. A camera that is sensitive to red and infrared light is used in this embodiment. In addition to the green fill, red lines are drawn at the edges of the veins 303, 304. Since the camera can see these red lines, the image enhancement software can look to see if the red lines are at the proper position and if needed automatic alignment can be performed. An alternative embodiment would be to paint a red line 306 down the middle of the vein position. An alternative embodiment would be to paint some pattern of red light over a desired portion of the vein.

Typically the cameras used in an LCE are monochrome and unable to discriminate between light of different wavelengths. Depending on the sensitivity of the camera and the brightness of the projector compared to the infrared flood lighting provided by the LCE, various techniques can be used to aid the camera in the detection of the red lines. One method is to simply look for the brightening caused by the addition of the red lines to the reflected infrared light. A second method is to periodically turn off the infrared lighting such that only ambient infrared and the projected red are seen by the camera. This can make it easier for the system to detect the red lines.

Although we've described the invention using red and green lights, various combinations of colors can be used. Red and infrared light are known in the art to be useful for vein detection. Any combinations of colors of shorter wavelengths can be used for projection and alignment images as long as the camera selected is properly selected or filtered to achieve the desired discrimination between wavelengths. Furthermore, while discrimination between projection, detection and alignment signals in the preferred embodiment has been described using different wavelengths to separate the signals, in an embodiment with less freedom of projected color, time division can be used where the projected image is shown most of the time and the alignment image is shown interspersed on a lower duty cycle basis. Properly implemented, the alignment image will be quite visible to the VCE's camera, but invisible to the operator of the VCE.

Projectors in VCEs can be either monochrome (e.g., projecting green only) or multicolor (e.g., projecting RGB). The advantage of a monochrome implementation is that since an array of single color LEDs can be used in place of white bulbs and a color wheel typically found in a multicolor projector the system can be of lower cost, generate less heat and have higher reliability. In such an embodiment, the time division scheme describe above would be appropriate. In this monochrome configuration, an alternative embodiment would be to add a smaller array of a second color of LEDs (i.e., red). This alignment array can be smaller than the projection array in that it doesn't need to be visible to the operator, just to the camera. The projection LEDs and the alignment LEDs could then be time multiplexed as previously described.

We claim:

1. A system, for use in vein imaging to ensure the proper alignment of a detected vein pattern and a visible projection of the vein pattern, said system comprising:
a light source configured to illuminate a field of view with a first wavelength of infrared light, to create an image contrast formed by the veins of the vein pattern and the surrounding tissue in the field of view undergoing differential amounts of absorption and reflection of said first wavelength of infrared light;
an alignment card positioned in the field of view, said alignment card comprising a material formed into a pattern, said material configured to emit a second wavelength of light when exposed to a visible light at a third wavelength, said third wavelength of light comprising a green color;
a camera, said camera configured to capture said image contrast of said reflected first wavelength of infrared light from the field of view;
a projector, said projector configured to project said captured image contrast onto the field of view using said visible light at said third wavelength; said camera configured to capture said second wavelength of light emitted by said pattern of material, and to capture said visible light at said third wavelength reflected from said pattern of material, said camera further configured to distinguish said wavelength of visible light at said third wavelength reflected by said pattern of material, from said second wavelength of light emitted by said pattern of material; and an image processing system, said image processing system configured to utilize said distinction between a reflection of a projected alignment card pattern at said third wavelength of light captured by said camera, and said second wavelength of emitted light from said alignment card pattern also captured by said camera, to thereby align said projected image with said reflected image contrast at said first wavelength of infrared light.

2. The system according to claim 1 wherein said material of said alignment card pattern comprises a fluorescent material.

3. The system according to claim 2 wherein said alignment card pattern comprises a known pattern.

4. The system according to claim 3 wherein said projected green light is used to fill the area in the field of view being outside of the veins of the vein pattern, wherein said projected green light goes to the edges of the veins.

5. The system according to claim 4 wherein said light source is a light source from the group of light sources consisting of: a laser; and a light emitting diode (LED).

6. The system according to claim 3 wherein said second wavelength of light comprises red light.

7. A vein contrast enhancer, for use in vein imaging and for ensuring the proper alignment of a vein pattern, detected as an image contrast reflected from a field of view, and a projection of the image contrast onto the field of view, said vein contrast enhancer comprising:
a light source configured to emit a first wavelength of infrared light directed onto the field of view, to create an image contrast formed by differential absorption and reflection of said first wavelength of infrared light by the veins of the vein pattern and the surrounding tissue in the field of view;
an alignment card comprising a material formed into a pattern, said material configured to emit a second wavelength of light when exposed to a visible light at a third wavelength, said third wavelength of light comprising a green color, said alignment card positioned within the field of view;
a camera, said camera configured to capture said image contrast of said reflected first wavelength of infrared light from the field of view;
a projector, said projector configured to project said captured image contrast onto the field of view using said visible light at said third wavelength, said camera configured to capture said second wavelength of light emitted by said pattern of material, and to capture said visible light at said third wavelength reflected from said pattern of material, said camera further configured to distinguish said wavelength of visible light at said third wavelength reflected by said pattern of material, from said second wavelength of light emitted by said pattern of material; and wherein said projector is configured to perform image processing, with said projector configured to utilize said distinction between a reflection of a projected alignment card pattern at said third wavelength of light captured by said camera, and said second wavelength of emitted light from said alignment card pattern also captured by said camera, to align said projected image, with said reflected image contrast at said first wavelength of infrared light.

8. The vein contrast enhancer according to claim 7 wherein said second wavelength of light comprises red light.

9. The vein contrast enhancer according to claim 7 wherein said projected green light is used to fill the area in the field of view being outside of one or more veins of the vein pattern with said projected green light going to the edges of the veins.

10. The vein contrast enhancer according to claim 7 wherein said source of infrared light is a light source from the group of light sources consisting of: a laser; and a light emitting diode (LED).

11. The vein contrast enhancer according to claim 7 wherein said material of said alignment card pattern comprises a fluorescent material.

12. The vein contrast enhancer according to claim 11 wherein said alignment card pattern comprises a known pattern.

* * * * *